United States Patent [19]

Vanmeter et al.

[11] 4,410,618

[45] Oct. 18, 1983

[54] BLOCKED PHOTOGRAPHIC REAGENTS

[75] Inventors: James P Vanmeter; Chin H. Chen, both of Rochester, N.Y.

[73] Assignee: Eastman Kodak Company, Rochester, N.Y.

[21] Appl. No.: 387,398

[22] Filed: Jun. 11, 1982

[51] Int. Cl.³ .............. G03C 1/40; G03C 1/10; G03C 5/54; G03C 7/00
[52] U.S. Cl. .............. 430/219; 430/218; 430/239; 430/382; 430/390; 430/428; 430/434; 430/443; 430/446; 430/454; 430/505; 430/544; 430/559; 430/566; 430/598; 430/955; 430/956; 430/957; 430/958; 430/959; 430/960
[58] Field of Search .............. 430/212, 218, 219, 223, 430/443, 568, 544, 446, 955, 956, 957, 958, 959, 960, 559, 564, 570, 598, 505, 236, 239, 428, 434, 382, 390, 383, 454

[56] References Cited

U.S. PATENT DOCUMENTS

| | | | |
|---|---|---|---|
| 3,615,432 | 10/1971 | Jenkins et al. | 430/581 |
| 4,063,950 | 12/1977 | Fujiwhara et al. | 96/66.3 |
| 4,124,392 | 11/1978 | Adin et al. | 430/211 |
| 4,144,063 | 3/1979 | Haas | 430/211 |
| 4,226,934 | 10/1980 | Webb et al. | 430/443 |
| 4,263,393 | 4/1981 | Chen | 430/443 |
| 4,350,752 | 9/1982 | Reczek et al. | 430/219 |

*Primary Examiner*—Richard L. Schilling

*Attorney, Agent, or Firm*—Harold E. Cole

[57] ABSTRACT

α-Ketoimidomethyl blocked photographic reagents are useful in photographic elements, film units and processes. The blocked photographic reagents have the structure:

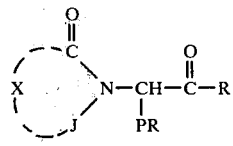

wherein
J represents

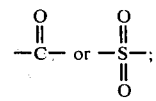

X represents the atoms to complete a 5- or 6-membered ring or ring system;
R represents alkyl of 1 to 30 carbon atoms or aryl of 6 to 30 carbon atoms; and
PR represents the residue of an organic photographic reagent containing a heteroatom through which it is joined to the blocking group.

21 Claims, No Drawings

BLOCKED PHOTOGRAPHIC REAGENTS

This invention relates to novel blocked photographic reagents and to photographic elements, film units and processes employing them.

It is frequently advantageous to have a photographic reagent present during the processing of a photographic element. The reagent can lead to a number of desirable effects depending upon the nature of the reagent, the point in time at which it is made available in the process and the nature of other components in the photographic element. For example, development inhibitors (also referred to in the art as development restrainers and development arrestors) can be introduced into photographic elements to provide improvements in granularity and/or reductions in background density.

A highly useful way of making a photographic reagent available is to incorporate it in the element so that it will be available at a desired point in time during processing. If incorporated in its active form, the photographic reagent can prematurely interact with other components in the element, e.g., during storage or prior to the particular point in time during processing at which it will provide an optimum effect. A technique which can be employed to avoid these difficulties is to block the photographic reagent with a group which converts it to an inactive form and incorporate the blocked photographic reagent in the element.

Useful blocking groups should satisfy a number of often contradictory requirements. They should be stable under storage conditions; they should unblock and make available the photographic reagent rapidly and in a controlled manner at the desired point in the process; they should preferably be inexpensive to make and use simple uncomplicated chemistry; and they should not give rise to unwanted by-products which would have an adverse effect on the process or the final image.

Accordingly, it would be desirable to provide photographic reagents blocked with relatively simple groups, the photographic reagents being stable on storage, yet unblocking in a controlled manner during processing to yield the photographic reagent and innocuous by-products.

We have found that certain α-ketoimidomethyl groups are highly effective in blocking photographic reagents for use in photographic elements and image transfer film units. These blocking groups can be employed to block development inhibitors or restrainers as well as other photographic reagents. Under the alkaline conditions encountered during photographic processing, these blocking groups are uniformly cleaved from the photographic reagent, thus converting the reagent to its active form. It is surprising that the reagent is released uniformly, since a carbonyl group adjacent a methyl or methylene group would be expected to activate the latter group and lead to imagewise release, as described in U.S. Pat. Nos. 4,063,950 and 4,226,934.

In accordance with one aspect of this invention there are provided blocked photographic reagents having the structure:

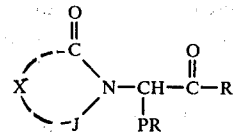

wherein:
J represents

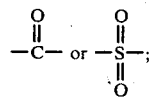

X represents the atoms to complete a heterocyclic nucleus containing at least one 5- or 6-membered ring;

R represents hydrogen, alkyl of 1 to 30 carbon atoms or aryl of 6 to 30 carbon atoms; and PR represents the residue of an organic photographic reagent containing a heteroatom through which it is joined to the α-ketoimidomethyl blocking group.

In another aspect this invention relates to a photographic element comprising a support bearing a silver halide emulsion layer having associated therewith a blocking photographic reagent as described above.

In yet another aspect this invention relates to an image transfer film unit comprising (a) a photosensitive element comprising a support bearing a layer of a silver halide emulsion having associated therewith a dye-image-providing material, and (b) a dye image-receiving layer, the film unit containing a blocked photographic reagent as described above.

In still another aspect this invention relates to processes of forming photographic images with photographic elements and film units as described above.

In the above structural formula I, the moiety X, together with the group represented by J, can complete a mono-, bi- or tricyclic ring or ring system each ring of which contains 5 to 6 members. Preferred ring systems are the phthalimide (1,3-isoindolinedione) ring system and the saccharin (1,2-benzisothiazolin-3-one-1,1-dioxide) ring system. Other useful ring systems includes succinimide, maleimide, hydantoin, 2,4-thiazolidinedione, hexahydro-2,4-pyrimidinedione, 1,4-dihydrophthalimide, and the like. These rings can be unsubstituted or substituted with a group or groups which render the material nondiffusible in a photographic element, enhance diffusibility, or modify the rate of unblocking. Representative substituents include halogen, nitro, alkyl, aryl, alkenyl, alkoxy, aryloxy, alkenyloxy, alkylcarbonyl, arylcarbonyl, alkenylcarbonyl, alkylsulfonyl, arylsulfonyl, alkenylsulfonyl, amino, aminocarbonyl, aminosulfonyl, carboxy, alkoxycarbonyl, aryloxycarbonyl, alkenyloxycarbonyl and the like. The alkyl portions of these substituents contain from 1 to about 30 carbon atoms, the alkenyl portions of these substituents contain from 2 to about 30 carbon atoms, and the aryl portions of these substituents contain from 6 to about 30 carbon atoms. The alkyl, aryl and alkenyl portions of these substituents can be further substituted with groups of the type specified above. Thus, alkyl is inclusive of, e.g., aralkyl and aryloxyalkyl, aryl is inclusive of, e.g., alkaryl and alkoxyaryl, and alkenyl is inclusive of e.g., aralkenyl. The amine portions of these substituents include primary, secondary and tertiary amines.

The alkyl and aryl groups represented by R can be unsubstituted or substituted with substituents as described above. Preferred are aryl groups substituted with alkyl or aryl groups. Representative R groups include phenyl, naphthyl, tolyl, xylyl, p-hexylphenyl, p-nonylphenyl, p-decylphenyl, p-biphenyl, methyl, ethyl, propyl, octyl, dodecyl, octadecyl and the like.

The photographic reagent represented by PR can be any organic photographic reagent which is usefully released in a photographic element and which contains a hetero atom available for blocking. A photographic reagent is a compound or moiety which, upon unblocking, is capable of reacting with another component of the element or film unit. The photographic reagent can contain a carrier group (described in more detail hereinafter in connection with dye releasing compounds) which is detached from the reagent as a function (either direct or inverse) of silver halide development and thereby renders the photographic reagent diffusible. Such photographic reagents are highly useful when it is desired to have the reagent act in an imagewise fashion in a layer of the element or film unit other than that in which it is coated. During processing of the element the reagent is uniformly unblocked, converting it to its active form, yet remains nondiffusible except in those areas where it is detached from the carrier as a function of silver halide development.

Particularly preferred photographic reagents are development inhibitors, such as mercaptotetrazoles and benzotriazoles, in which a sulfur or nitrogen atom is blocked with a blocking group in accordance with this invention. Other useful photographic reagents contain sulfur, oxygen, selenium, nitrogen or phosphorous atoms available for derivatization with the blocking group. Such reagents include developing agents and electron transfer agents such as hydroquinones, aminophenols, p-phenylenediamines and pyrazolidones; silver halide solvents, complexing agents or fixing agents such as triazinethiones and thiazolinethiones; and fogging or nucleating agents such as hydrazines and hydrazides. The blocking groups of this invention are particularly useful with photographic reagents which have a pKa of about 2 to about 6 (pka being the pH of an aqueous solution of the unblocked reagent half neutralized by alkali and measured as described in E. Kosower, *Introduction To Physical Organic Chemistry*, N.Y., John Wiley And Sons, 1968, Chapter 1.)

In addition to blocking photographic reagents, the blocking groups of the present invention can be employed to block photographic dyes and dye release compounds. The blocking group can be attached to any hetero atom in the dye available for derivatization, so as to shift the spectral absorption of the dye or to prevent the group to which it is attached from undergoing unwanted side reactions. The blocking groups of this invention are preferably attached to acidic hydroxy groups or to carboxy groups.

Preferred blocked photographic reagents of this invention have the structural formulae:

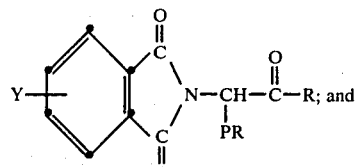

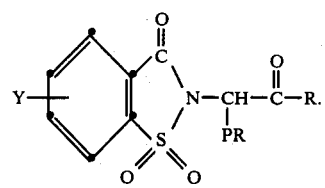

wherein:

R and PR are as defined above; and

Y is hydrogen or one or more substituents selected from the group consisting of halogen, nitro, alkyl, aryl, alkenyl, alkoxy, aryloxy, alkenyloxy, alkylcarbonyl, arylcarbonyl, alkenylcarbonyl, alkylsulfonyl, arylsulfonyl, alkenylsulfonyl, amino, aminocarbonyl, aminosulfonyl, carboxy, alkoxycarbonyl, aryloxycarbonyl, alkenyloxycarbonyl and the like; the alkyl, alkenyl and aryl portions of these substituents being as defined above.

Preferred blocked photographic reagents of this invention are shown in Table I, below.

TABLE I

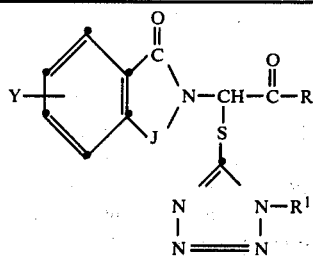

| Compound | J | Y | R | R¹ |
|---|---|---|---|---|
| 1 | SO$_2$ | H | —C$_6$H$_4$—p-C$_6$H$_5$ | —C$_6$H$_5$ |
| 2 | SO$_2$ | H | —C$_6$H$_5$ | —C$_6$H$_5$ |
| 3 | SO$_2$ | H | —C$_6$H$_5$ | m-CH$_3$SO$_2$NHC$_6$H$_4$ |
| 4 | CO | H | —C$_6$H$_5$ | —C$_6$H$_5$ |
| 5 | CO | H | —C(CH$_3$)$_3$ | —C$_6$H$_5$ |
| 6 | SO$_2$ | H | —C$_6$H$_4$—p-C$_6$H$_5$ | m-CH$_3$SO$_2$NHC$_6$H$_4$ |
| 7 | SO$_2$ | H | —C$_6$H$_4$—p-(n-C$_9$H$_{19}$) | —C$_6$H$_5$ |
| 8 | SO$_2$ | H | —C$_6$H$_5$ | —C$_2$H$_5$ |
| 9 | SO$_2$ | H | —C$_6$H$_5$ | (see (a) below) |
| 10 | CO | 4-(i-C$_3$H$_7$)NHSO$_2$— | —C$_6$H$_5$ | —C$_6$H$_5$ |
| 11 | SO$_2$ | H | C$_6$H$_5$ | m-CH$_3$CONHC$_6$H$_4$— |
| 12 | SO$_2$ | H | —C$_6$H$_4$—p-C$_6$H$_5$ | —C$_2$H$_5$ |

TABLE I-continued

![structure with Y, J, N-CH-C(=O)-R, S-tetrazolyl-R¹]

| Compound | J   | Y | R                      | R¹                     |
|----------|-----|---|------------------------|------------------------|
| 13       | SO₂ | H | —C₆H₄—p-(n-C₉H₁₉)      | —C₂H₅                  |
| 14       | SO₂ | H | —C₆H₄—p-(n-C₁₀H₂₁)     | —C₆H₅                  |
| 15       | SO₂ | H | —C₆H₄—p-C₆H₅           | m-CH₃SO₂NHC₆H₄—        |

(a) Compound 9 has a 2-benzimidazolylthio group in place of a tetrazolylthio group.

The photographic reagents to be blocked in accordance with this invention are known compounds. Similarly precursors of the α-ketoimidomethyl blocking groups of this invention are known compounds. The photographic reagents can be derivatized with the blocking group by reaction of an alkali metal salt of the reagent with an α-halo derivative of the α-ketomethylimide. The α-halo derivative can be prepared by reaction of the α-ketomethylimide with elemental halogen or with an acid halide. A representative technique for preparing blocked photographic reagents is shown in the preparative examples, infra.

The blocked photographic reagents of this invention have good storage stability but readily unblock in the alkaline environment encountered during photographic processing. While not wishing to be bound to any theory, it is believed that the blocking group is removed by an elimination reaction initiated by electrophilic attack of hydroxide ion under alkaline conditions. The following reaction scheme illustrates the reaction sequence which is believed to lead to release of the photographic reagent.

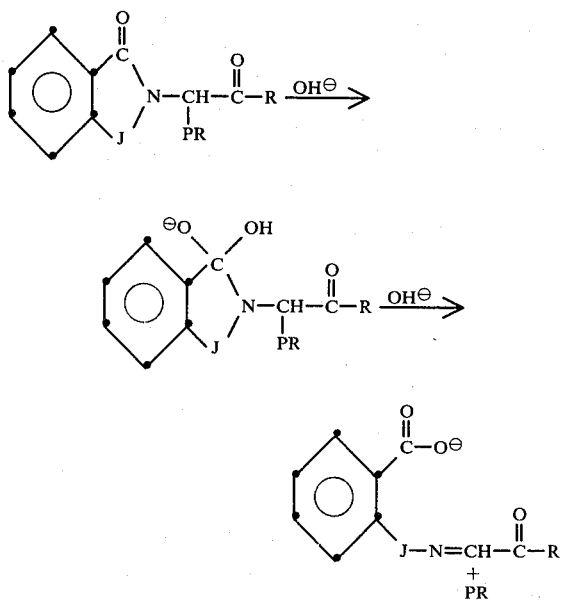

The rate at which the photographic reagent is released will vary depending upon the nature of the ring and the substituents thereon. Thus the invention provides a family of compounds which can release the same photographic reagent at different rates depending upon particular needs in a given photographic material. In general, electron-withdrawing substituents, such as nitro, aminocarbonyl and aminosulfonyl, lead to more rapid release whereas electron-donating substituents, such as alkyl and alkoxy, lead to slower release.

The blocked photographic reagents of this invention can be employed with photographic elements and film units in the ways and for the purposes which photographic reagents have previously been employed with photographic elements and film units. For example, if the reagent is a development inhibitor, it can be used to suppress development of silver halide. If the photographic reagent is a bleach inhibitor, it can be used to inhibit bleaching of silver during a subsequent processing step. If the photographic reagent is a silver halide solvent or complexing agent, it can be used to enhance removal of silver halide from the element or film unit during a subsequent processing step or to assist migration of silver halide in the element or film unit. If the photographic reagent is an auxiliary developing agent, it can be used to assist development of silver halide. If the photographic reagent is a spectral sensitizing dye, it can be used to render silver halide differentially sensitive to exposure to electromagnetic radiation which occurs contemporaneous with or subsequent to release of the reagent. Still other ways in which the released photographic reagent can be employed in photographic elements, film units and processes will be apparent to those skilled in the art.

The blocked photographic reagents can be incorporated in photographic elements and film units by techniques available in the art. In certain preferred embodiments the blocked photographic reagent is first dissolved in a high-boiling solvent, such as a water-insoluble coupler solvent, and then dispersed in a carrier material. Typical useful coupler solvents are moderately polar solvents such as tri-o-tolyl phosphate, di-n-butyl phthalate, diethyl lauramide, 2,4-diamylphenol, liquid dye stabilizers such as described in an article entitled "Improved Photographic Dye Image Stabilizer-Solvent", *Product Licensing Index*, Vol 83, March, 1971, and the like. (*Product Licensing Index* is published by Industrial Opportunities Ltd., Homewell, Havant Hampshire, P09 1EF, United Kingdom.)

Depending upon the particular photographic reagent, and the purpose for which it is being used, it may be on a support separate from the photosensitive element (e.g., in a separate cover sheet, process sheet or receiver element) and be brought into contact with the photosensitive element during processing, it may be in a photosensitive layer of the photosensitive element or it may be in the photosensitive element or film unit but in a location other than a photosensitive layer (e.g., in an adjacent layer or in a layer of mask adhesive as described in Rose and Eldredge U.S. Application Ser. No. 208,746, entitled "Acid Adhesive Compositions And Self-Processing Photographic Products Containing Same", filed Nov. 20, 1980, now U.S. Pat. No. 4,357,408, issued Nov. 2, 1982, and in Bowman U.S. Application Ser. No. 208,747, entitled "Sulfo-Containing Adhesive Compositions And Self Processing Photographic Products Containing Same", filed Nov. 20, 1980, now U.S. Pat. No. 4,357,409, issued Nov. 2, 1982.) The optimum concentration of blocked photographic reagent will depend upon the location of the blocked reagent, the purpose for which it is used and the particular blocked reagent employed.

The photographic elements with which the blocked photographic reagents of this invention are employed can be simple elements comprising a support hearing a layer of a silver halide emulsion. Preferred elements are multilayer multicolor silver halide elements and especially preferred are color diffusion transfer film units.

A typical multilayer multicolor photographic element according to this invention can comprise a support having thereon a red-sensitive silver halide emulsion unit having associated therewith a cyan-dye-image-providing material, a green-sensitive silver halide emulsion unit having associated therewith a magenta-dye-image-providing material and a blue-sensitive silver halide emulsion unit having associated therewith a yellow-dye-image-providing material, there being associated with at least one of the silver halide emulsion units a blocked photographic reagent of this invention. Each silver halide emulsion unit can be composed of one or more layers and the various units and layers can be arranged in different relationships with respect to one another in accordance with configurations known in the art. In an alternative format, the emulsions sensitive to each of the three primary regions of the spectrum can be disposed as a single segmented layer, e.g., as by the use of microvessels as described in Whitmore U.S. patent application Ser. No. 184,714, now U.S. Pat. No. 4,362,806, issued Dec. 7, 1982.

The photographic film units of this invention comprise:

(1) a photographic element as described above; and
(2) a dye-image-receiving layer, the film unit containing a blocked photographic reagent of this invention.

The dye-image-receiving layer in the film unit can be integral with the photographic element or located on a separate support adapted to be superposed on the photographic element after exposure thereof.

Any material can be employed as the dye-image-receiving layer in the film units of this invention as long as it will mordant, or otherwise fix, the dye which diffuses to it. The particular material chosen will, of course, depend upon the dye or dyes to be mordanted. The dye image receiving layer can contain ultraviolet absorbers to protect the dye image from fading due to ultraviolet light, brighteners and similar materials to protect or enhance the dye image, and the like.

In a preferred embodiment, the film units of this invention contain an alkaline processing composition and means containing same for discharge of the alkaline processing composition within the film unit. A preferred means is a rupturable container which is adapted to be positioned during processing of the film unit so that a compressive force applied to the container by pressure-applying members, such as would be found in a camera designed for in-camera processing, will effect a discharge of the container's contents within the film unit. However, other methods of introducing the alkaline processing composition can be employed.

In a preferred embodiment, the film units of this invention contain a cover sheet on the opposite side of the photosensitive layers from the dye image-receiving layer and the film unit is adapted for discharge of the alkaline processing composition between the cover sheet and the photosensitive layers. A preferred cover sheet comprises a support bearing a neutralizing layer (also referred to as a pH lowering layer or acid layer) and at least one timing layer (also sometimes referred to as a spacer layer or "inert" spacer layer.) Suitable materials for use in the neutralizing and timing layers are described in *Research Disclosure*, Vol. 123, Item 12331, July 1974 and Vol. 135, Item 13525 July 1975. (*Research Disclosure* is published by Industrial Opportunities Limited, Homewell, Havant, Hampshire, P09, 1EF, U.K.). In an especially preferred film unit of this invention the blocked photographic reagent is a blocked development inhibitor contained in a timing layer of a cover sheet.

In addition to the layers referred to above, the elements and film units can contain additional layers conventional in photographic elements and film units, such as spacer layers, filter layers, antihalation layers, scavenger layers, pH lowering layers (sometimes referred to as acid layers and neutralizing layers), timing layers, opaque reflecting layer, opaque light-absorbing layers and the like. Useful supports include polymeric films, paper (including polymer-coated paper), glass and the like.

The light-sensitive silver halide emulsions employed in the photographic elements and film units can include coarse, regular or fine grain silver halide crystals or mixtures thereof and can be comprised of such silver halides as silver chloride, silver bromide, silver bromoiodide, silver chlorobromide, silver chloroiodide, silver chlorobromoiodide, and mixtures thereof. The emulsions can be negative working or direct positive emulsions. They can form latent images predominantly on the surface of the silver halide grains or in the interior of the silver halide grains. They can be chemically and spectrally sensitized in accordance with usual practices. The emulsions typically will be gelatin emulsions although other hydrophilic colloids can be used in accordance with usual practice. Details regarding the silver halide emulsions and addenda therein are contained in *Research Disclosure*, Item 17643, December 1978 and the references listed therein.

Depending upon the dye-image-providing material employed with the photographic element or film unit, it can be incorporated in the silver halide emulsion layer or in a separate layer associated with the emulsion layer. The dye-image-providing material can be any of a number known in the art, such as dye-forming couplers, dye developers and redox dye-releasers, and the particular one employed will depend on the nature of the element or film unit and the type of image desired. Materials useful in diffusion transfer film units contain a dye moiety and a monitoring moiety. The monitoring moiety, in the presence of an alkaline processing solution and as a function of silver halide development, is responsible for a change in mobility of the dye moiety. These dye image-providing materials can be initially mobile, and rendered immobile as a function of silver halide development, as described in U.S. Pat. No. 2,983,606. Alternatively, they can be initially immobile and rendered mobile, in the presence of an alkaline processing solution, as a function of silver halide development. This latter class of materials include redox dye-releasing compounds. In such compounds, the monitoring group is a carrier from which the dye is released as a direct function of silver halide development or as an inverse function of silver halide development. Compounds which release dye as a direct function of silver halide development are referred to as negative-working release compounds, while compounds which release dye as an inverse function of silver halide development are referred to as positive-working release compounds.

A preferred class of negative-working release compounds are the ortho or para sulfonamidophenols and naphthols described in U.S. Pat. No. 4,054,312, 4,055,428 and 4,076,529. In these compounds the dye moiety is attached to a sulfonamido group which is ortho or para to the phenolic hydroxy group and is released by hydrolysis after oxidation of the sulfonamido compound during development.

A preferred class of positive-working release compounds are the nitrobenzene and quinone compounds described in U.S. Pat. No. 4,139,379. In these compounds the dye moiety is attached to an electrophilic cleavage group, such as a carbamate group, ortho to the nitro group or the quinone oxygen, and is released upon reduction of the compound by an electron donor compound contained in the element or the processing composition, unless the electron donor is oxidized during development.

Other useful positive-working release compounds are the hydroquinones described in U.S. Pat. No. 3,980,479 and the benzisoxazolone compounds described in U.S. Pat. No. 4,199,354.

Further details regarding the above release compounds, the manner in which they function, and the procedures by which they can be prepared are contained in the patents referred to above, the disclosures of which are incorporated herein by reference.

After exposure, the photographic reagent is unblocked and an image is developed in the photographic elements and film units by treatment with an alkaline processing composition in the presence of a silver halide developing agent.

The effect which the unblocked photographic reagent will have on image formation will depend upon (1) the photographic reagent released, (2) the type of silver halide employed and (3) the type of dye-image-providing material employed.

With the photographic film units of the present invention, the alkaline environment provided permits the release of photographic reagent, the development of developable silver halide and an imagewise change in mobility of the dye-image-providing material. The diffusible dye can be transferred to an image receiving layer and employed as a transfer image. Alternatively, it can merely be removed from the element. Whether the diffusible dye is employed to form a transfer image or not, the remaining dye-image-providing material, from which dye has not been released, can be employed to form either a retained image or a transfer image by techniques well known to those skilled in the art.

The alkaline processing composition can be an aqueous solution of an alkaline material, such as an alkali metal hydroxide or carbonate (e.g., sodium hydroxide or sodium carbonate) or an amine (e.g. diethylamine). Preferably the alkaline composition has a pH in excess of 11. Suitable materials for use in such compositions are disclosed in *Research Disclosure*, pages 79–80, November 1976.

Preferably the developing agent is contained in the alkaline processing composition, although it can be contained in a separate solution or process sheet, or it can be incorporated in a layer of the photographic element or film unit. When the developing agent is separate from the alkaline processing composition, the alkaline composition serves to activate the developing agent and provide a medium in which the developing agent can contact and develop developable silver halide.

A variety of silver halide developing agents can be used in processing the elements and film units of this invention. The choice of a particular developing agent will depend on the type or film unit with which it is used and the particular dye image-providing material employed. Suitable developing agents can be selected from such compounds as hydroquinone, aminophenols (e.g., N-methylaminophenol), 1-phenyl-3-pyrazolidone, 1-phenyl-4,4-dimethyl-3-pyrazolidone, 1-phenyl-4-methyl-4-hydroxymethyl-3-pyrazolidone, N,N,N',N'-tetramethyl-p-phenylenediamine, etc. The non-chromogenic developers in this list are preferred for use in diffusion transfer film units, since they have a reduced propensity to stain dye image-receiving layers.

Various formats for diffusion transfer film units are known in the art. The layer arrangement employed with them can be used in this invention. In one useful format, the dye image receiving layer is located on a separate support adapted to be superposed on the photographic element after exposure thereof. Such image receiving layers are generally disclosed, for example, in U.S. Pat. No. 3,362,819.

In another useful format, the dye image receiving layer is located integral with the photographic element and is positioned between the support and the lowermost silver halide emulsion layer. One such format is disclosed in Belgian Pat. No. 757,960. In such a format, the support for the photographic element is transparent and bears in order, an image receiving layer, a substantially opaque light-reflective layer, and then the photosensitive layer or layers. After imagewise exposure, a rupturable container containing the alkaline processing composition and an opaque process sheet are brought into superposed position. Pressure-applying members in the camera rupture the container and spread processing composition over the photographic element as the assemblage is withdrawn from the camera. The processing composition develops each exposed silver halide emulsion layer and dye images, formed as a function of development, diffuse to the image receiving layer to provide a right-reading image which is viewed through the transparent support on the opaque reflecting layer backgrounds. For other details concerning the format of this particular integral film unit, reference is made to the above mentioned Belgian Pat. No. 757,960.

Another format is disclosed in Belgian Pat. No. 757,959. In this embodiment, the support for the photographic element is transparent and bears, in order, the image-receiving layer, a substantially opaque, light-reflective layer and the photosensitive layer or layers. A rupturable container, containing an alkaline processing composition and an opacifier, is positioned between the uppermost emulsion layer and a transparent cover sheet which has thereon a neutralizing layer and a timing layer. The assemblage is placed in a camera, exposed through the transparent cover sheet and then passed through a pair of pressure-applying members in the camera as it is being removed therefrom. The pressure-applying members rupture the container and spread processing composition and opacifier over the photographic layers to commence development and protect the photosensitive layers from further light exposure. The processing composition develops each silver halide layer and dye images, formed as a result of development, diffuse to the image receiving layer to provide a right-reading image which is viewed through the transparent support on the opaque reflecting layer background. For further details concerning the format of this particular integral assemblage, reference is made to the above-mentioned Belgian Pat. No. 757,959.

Still other useful formats in which this invention can be employed are described in U.S. Pat. Nos. 3,415,644; 3,415,645; 3,415,646; 3,647,437; 3,635,707; and 3,993,486. Further details regarding diffusion transfer film units are contained in Research Disclosure, Vol. 151, Item 15162, November 1976.

The term "nondiffusible" used herein has the meaning commonly applied to the term in photography and denotes materials that for all practical purposes do not migrate nor wander through organic colloid layers such as gelatin in an alkaline medium, in photographic elements and preferably when processed in a medium having a pH of 11 or greater. The same meaning is to be attached to the term "immobile". The term "diffusible" has the converse meaning and denotes the materials having the property of diffusing effectively through the colloid layers of photographic elements in an alkaline medium. "Mobile" has the same meaning.

The term "associated therewith" as used herein is intended to mean that the materials can be in either the same or different layers so long as the materials are accessible to one another during processing.

The following examples further illustrate this invention.

PREPARATIVE EXAMPLE 1

Preparation of
N-[α-(1-Phenyl-5-tetrazolylthio)p-phenylphenacyl]saccharin (Compound 1)

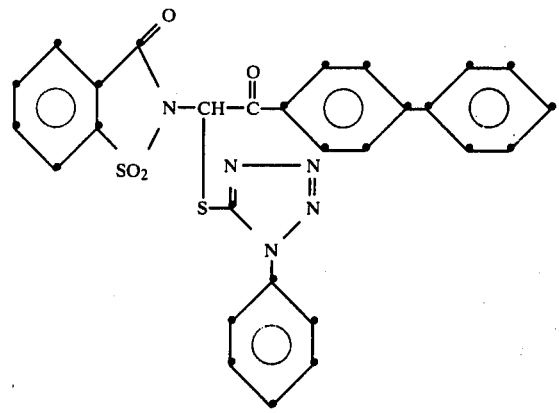

To N-(p-Phenylphenacyl)saccharin (25 g) in acetic acid (100 ml) was added bromine (15.8 g). The reaction mixture was heated on a steam bath for 2¼ hours. The reaction mixture was evaporated to dryness under vacuum and the solid product was washed with water and air dried to give the α-bromo derivative (28.9 g), m.p. 250°-254° C. This intermediate was reacted with the sodium salt of 1-phenyl-1H-tetrazole-5-thiol (16.8 g) in N,N-dimethylformamide (100 ml) for 30 hours at room temperature. The reaction mixture was then poured into ice-water. The crude product was removed by filtration and purified by column chromatography on silica gel using methylene chloride as the solvent, followed by several recrystallizations from methylene chloride/ethanol to give the title product (26.5 g), m.p. 112°-115° C.

PREPARATIVE EXAMPLE 2

Preparation of
N-{α[1-(m-Methanesulfonamidophenyl)-5-tetrazolylthio]phenacyl}saccharin, (Compound 3)

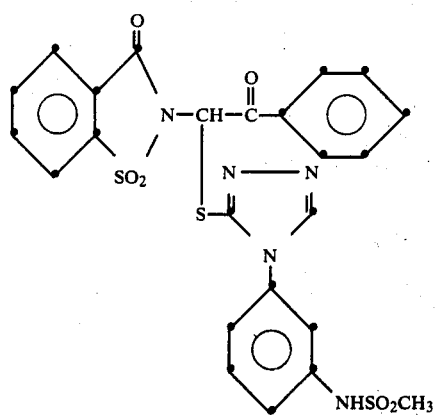

To a stirred mixture of N-phenacylsaccharin (100 g) in acetic acid (750 ml) heated on a steam bath was added bromine (70 g) in acetic acid (100 ml) over a period of 3 hours. After cooling slowly to room temperature, the reaction mixture was stored overnight at 10° C. The product was filtered, washed with acetic acid, then water, and air dried to give the α-bromo derivative (99.7 g), m.p. 168°-171° C.

To a solution of 1-(m-methanesulfonamidophenyl)-1H-tetrazole-5-thiol (14.7 g) in tetrahydrofuran (250 ml) was added a solution of potassium bicarbonate (5.7 g) in water (25 ml). After stirring for 2 hours, N-(α-bromophenacyl)-saccharin (20.0 g) was added and the reaction mixture was evaporated almost to dryness, the residue was treated with anhydrous sodium sulfate and the product was taken up in 20 percent tetrahydrofuran in methylene chloride and chromatographed on silica gel in the same solvent. The product was then recrystallized from a mixture of acetone cyclohexane containing a small amount of methylene chloride to give the title product (22.4 g), m.p. 173°-175° C.

PREPARATIVE EXAMPLE 3

Preparation of
N-[α-(1-phenyl-5-tetrazolylthio)phenacyl]phthalimide
(Compound 4)

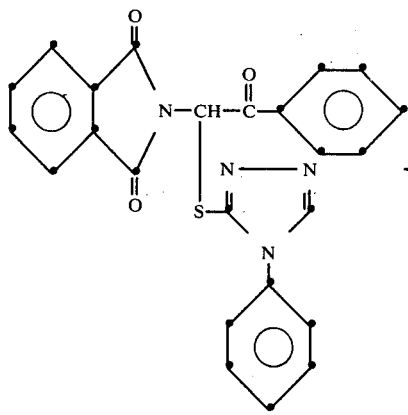

To a stirred solution of N-phenacylphthalimide (5.3 g) in methylene chloride (50 ml) containing a small amount of hydrobromic acid was added dropwise an equimolar amount of bromine in methylene chloride (10 ml). After the reaction was completed, the solvent was removed and the residue was crystallized from toluene to give the α-bromo derivative (5.4 g). To the α-bromo compound (5.5 g) in 2-butanone was added 40% Triton B surfactant in methanol (0.5 ml) and 2 equivalents of 1-phenyl-1H-tetrazole-5-thiol sodium salt. After stirring at room temperature for 18 hours, the reaction mixture was poured into dilute aqueous sodium bicarbonate. The solid was collected by filtration and recrystallized from methanol to give the title product (4.0 g, m.p. 170°–174° C.).

EXAMPLE 1

Release rates of blocked development inhibitors, prepared as in Preparative Example 1, were determined electrochemically using a streaming mercury electrode. A dispersion of each blocked inhibitor was prepared in tritolyl phosphate solvent at ratio of inhibitor:solvent of 1:3. A dilute aliquot, 2.5 ml, of the dispersion equivalent to 0.04 mmoles was then added to 4.75 ml of 0.1 N sodium hydroxide (pH 13). The current was measured as a function of time at 35° C. to determine the release rate (k) of the inhibitor. As a control, the blocked inhibitor, 5-(2-cyanoethylthio)-1-phenyltetrazole shown in U.S. Pat. No. 4,009,029, issued Feb. 22, 1977, was also evaluated. The release rates are shown below in Table II. The data show that with this blocking group a wide range of release rates can be obtained. Table II also rereports $t_{\frac{1}{2}}$ values, i.e. the time required for the concentration of the compound to drop to half of the original concentration.

TABLE II

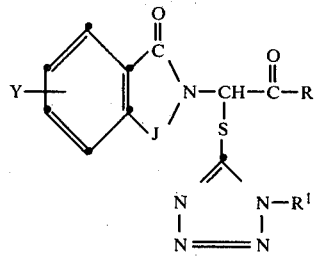

| Compound | J | R | R$^1$ | k(l/sec) | t$_{\frac{1}{2}}$ (sec) |
|---|---|---|---|---|---|
| Control | | | | 0.15 | 4.4 |
| 1 | SO$_2$ | —C$_6$H$_4$—p-C$_6$H$_5$ | —C$_6$H$_5$ | 0.15 | 4.6 |
| 2 | SO$_2$ | —C$_6$H$_5$ | —C$_6$H$_5$ | 0.19 | 3.6 |
| 3 | SO$_2$ | —C$_6$H$_5$ | m-CH$_3$SO$_2$NH—C$_6$H$_4$ | 0.16 | 4.3 |
| 4 | CO | —C$_6$H$_5$ | —C$_6$H$_5$ | 0.0052 | 133.0 |
| 5 | CO | —C(CH$_3$)$_3$ | —C$_6$H$_5$ | 0.39 | 1.7 | k = First order rate constant at pH 13, 35° C.
t$_{\frac{1}{2}}$ = Time for release of 50% inhibitor

EXAMPLE 2

This example shows that improved magenta dye stability is obtained when a blocked development inhibitor of the invention replaces a prior art blocked development inhibitor in the cover sheet of an image transfer element.

A photosensitive element using internal image reversal silver halide emulsions and sulfonamidonaphthol dye releasers is prepared equivalent to Example 5 of U.S. Pat. No. 4,209,580 of McCreary et al. The magenta dye releaser has the structure:

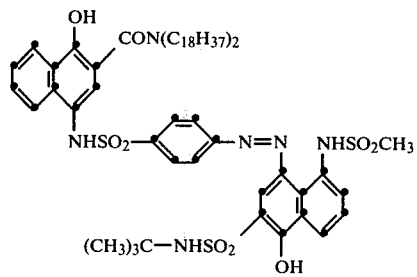

A control cover sheet is prepared by coating on a clear polyester support the following layers, in sequence:
1. Acid layer:
Poly(n-butyl acrylate-co-acrylic acid) at a 30:70 weight ratio equivalent to 140 meq acid.m$^2$.
2. Timing Layer:
1:1 Physical mixture of the following two polymers coated at 4.3 g/m$^2$
Poly(acrylonitrile-co-vinylidene chloride-co-acrylic acid) at a 18:75:7 weight ratio.

The carboxy ester lactone formed by cyclization of a vinyl acetate-maleic anhydride copolymer in the presence of 1-butanol to produce a partial butyl ester ratio of acid:ester of 15:85.

Comparison and inventive cover sheets are prepared which differ from the control only in that the comparison cover sheet contains 0.11 g/m² of the prior art blocked development inhibitor precursor 5-(2-cyanoethylthio)-1-phenyltetrazole described in U.S. Pat. No. 4,009,029 and the timing layer of the inventive cover sheet contains 0.23 g/m² (an equimolar amount) of Compound 2.

Separate samples of the photosensitive element are exposed in a sensitometer through a step-tablet to yield a neutral at a Status A density of 1.0. Individual samples are then processed at 16° C., 22° C. and 35° C. by spreading a viscous processing composition (identified below) between the sample and one of the transparent cover sheets described above using a pair of juxtaposed rollers to provide a processing gap of 65 μm. The assembled photosensitive element, plus cover sheet, is incubated at 38° C. for 14 days and the Status A density is read. A step that has a green density of 1.6 is selected for re-reading after the assembled unit is further incubated for a period of 7 days at 60° C./70%RH. The difference in Status A green density between the readings at 14 days and 21 days is a measure of the relative dark fade. The results are reported in Table III below.

The processing composition employed is as follows:

| | |
|---|---|
| Potassium hydroxide (45 percent aqueous solution) | 104 g |
| Sodium sulfite | 1.0 g |
| 5-Methylbenzotriazole | 4 |
| 1-p-Tolyl-4-methyl-3-pyrazolidinone | 12.8 g |
| 1,4-Cyclohexanedimethanol | 1 g |
| Sodium salt of naphthalene formaldehyde condensate (Tamol SN ®) | 6.4 g |
| Potassium fluoride.2 H₂O | 10.0 g |
| Carboxymethylcellulose | 44.0 g |
| Water to 1 liter | |

TABLE III

| | | | Green density loss after incubation Processing Temperature | | |
|---|---|---|---|---|---|
| Cover Sheet | Addenda | g/m² | 16° C. | 22° C. | 35° C. |
| Control | None | — | −0.05 | −0.06 | −0.14 |
| Comparison | | 0.11 | −0.14 | −0.16 | −0.06 |
| Invention | Compound 2 | 0.23 | −0.06 | −0.06 | −0.07 |

These data show that the comparison cover sheet, with the prior art blocked development inhibitor 5-(2-cyanoethylthio-1-phenyltetrazole) which releases an acrylonitrile fragment when the inhibitor is unblocked shows a loss in green density more than twice as great as the inventive cover sheet containing Compound 2. The inventive cover sheet has a green density loss equal to the control cover sheet, which does not contain any blocked development inhibitor.

The invention has been described in detail with particular reference to certain preferred embodiments thereof, but it will be understood that variations and modifications can be effected within the spirit and scope of the invention.

What is claimed is:

1. A photographic image transfer film unit comprising:
   (a) a photosensitive element comprising a support bearing a layer of a silver halide emulsion having associated therewith a dye-image-providing material, and
   (b) a dye image-receiving layer, the film unit containing an α-ketoimidomethyl blocked photographic reagent having the structure:

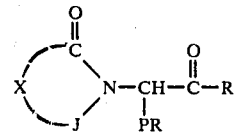

wherein:
J represents

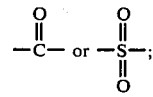

X represents the atoms to complete a heterocyclic nucleus containing at least one 5- or 6-membered ring;
R represents alkyl of 1 to 30 carbon atoms or aryl of 6 to 30 carbon atoms; and
PR represents the residue of a development inhibitor containing a sulfur or nitrogen atom through which it is joined to the α-ketoimidomethyl blocking group.

2. A photographic image transfer film unit comprising
   (a) a photosensitive element comprising a support having thereon a red-sensitive silver halide emulsion unit having associated therewith a cyan-dye-image-providing material, a green-sensitive silver halide emulsion unit having associated therewith a magenta-dye-image-providing material and a blue-sensitive silver halide emulsion unit having associated therewith a yellow-dye-image-providing material; and
   (b) a dye-image-receiving layer; the film unit containing an α-ketoimidomethyl blocked photographic reagent having the structure:

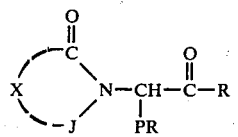

wherein:
J represents

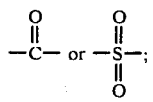

X represents the atoms to complete a heterocyclic nucleus containing at least one 5- or 6-membered ring;
R represents alkyl of 1 to 30 carbon atoms or aryl of 6 to 30 carbon atoms; and PR represents the residue of a development inhibitor containing a sulfur or nitrogen atom through which it is joined to the α-ketoimidomethyl blocking group.

3. A film unit of claim 2 further comprising an alkaline processing composition and means containing same for discharge of the alkaline processing composition within the film unit.

4. A film unit of claim 3 wherein the blocked photographic reagent is in or adjacent a silver halide emulsion layer.

5. A film unit of claim 3 further comprising a transparent cover sheet on the opposite side of the silver halide emulsion layers from the dye image receiving layer, and the means containing the alkaline processing composition being positioned for discharge of the alkaline processing composition between the cover sheet and the silver halide emulsion layers.

6. A film unit of claim 5 wherein the cover sheet comprises a transparent support bearing, in order, a neutralizing layer and a timing layer.

7. A film unit of claim 6 wherein the blocked photographic reagent is in a timing layer of the cover sheet.

8. A film unit of claim 2 wherein the dye-image-providing materials are redox dye-releasing compounds.

9. A film unit of claim 8 wherein the silver halide emulsions are direct positive emulsions and the redox dye releasing compounds are negative-working.

10. A film unit of claim 8 wherein the silver halide emulsions are negative emulsions and the redox dye-releasing compounds are positive-working.

11. A film unit of one of claims 1 through 10 wherein the α-ketoimidomethyl blocked photographic reagent has one of the structures:

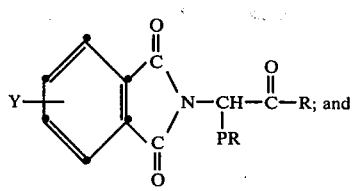

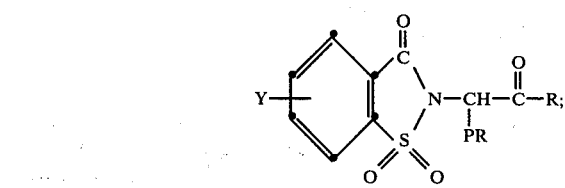

wherein:
R represents alkyl of 1 to 30 carbon atoms or aryl of 6 to 30 carbon atoms;
PR represents the residue of a development inhibitor containing a sulfur or nitrogen atom through which it is joined to the α-ketoimidomethyl blocking group; and
Y is hydrogen or one or more substituents selected from the group consisting of halogen, nitro, alkyl, aryl, alkenyl, alkoxy, aryloxy, alkenyloxy, alkylcarbonyl, arylcarbonyl, alkenylcarbonyl, alkylsulfonyl, arylsulfonyl, alkenylsulfonyl, amino, aminocarbonyl, aminosulfonyl, carboxy, alkoxycarbonyl, aryloxycarbonyl and alkenyloxycarbonyl.

12. A film unit of any one of claims 1 through 10 wherein the α-ketoimidomethyl blocked photographic reagent has the structure:

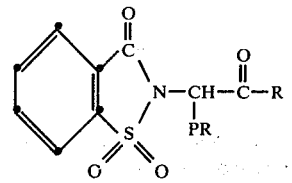

wherein:
R represents aryl of 6 to 30 carbon atoms; and
PR represents the residue of a development inhibitor containing a sulfur or nitrogen atom through which it is joined to the α-ketoimidomethyl blocking group.

13. A photographic element comprising a support bearing a photosensitive silver halide emulsion having associated therewith an α-ketoimidomethyl blocked photographic reagent having the structure:

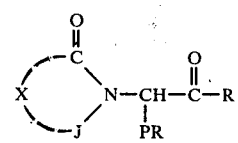

wherein:
J represents

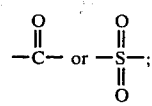

X represents the atoms to complete a heterocyclic nucleus containing at least one 5- or 6-membered ring;
R represents alkyl of 1 to 30 carbon atoms or aryl of 6 to 30 carbon atoms; and
PR represents the residue of a development inhibitor containing a sulfur or nitrogen atom through which it is joined to the α-ketoimidomethyl blocking group.

14. A photographic element comprising a support having thereon a red-sensitive silver halide emulsion unit having associated therewith a cyan-dye-image-providing material, a green-sensitive silver halide emulsion unit having associated therewith a magenta-dye-image-providing material and a blue-sensitive silver halide emulsion unit having associated therewith a yellow-dye-image providing material, there being associated with at least one of the silver halide emulsion units an α-ketoimidomethyl blocked photographic reagent having the structure:

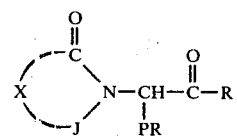

wherein:
J represents

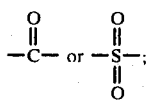

X represents the atoms to complete a heterocyclic nucleus containing at least one 5- or 6-membered ring;

R represents alkyl of 1 to 30 carbon atoms or aryl of 6 to 30 carbon atoms; and

PR represents the residue of a development inhibitor containing a sulfur or nitrogen atom through which it is joined to the α-ketoimidomethyl blocking group.

15. A photographic element of any one of claims 13 or 14 wherein the α-ketoimidomethyl blocked photographic reagent has one of the structures:

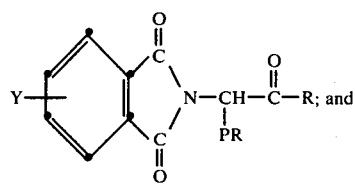

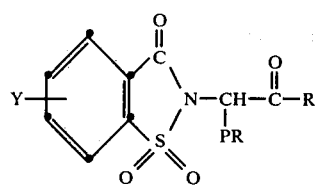

wherein:
  R represents alkyl of 1 to 30 carbon atoms or aryl of 6 to 30 carbon atoms;
  PR represents the residue of a development inhibitor containing a sulfur or nitrogen atom through which it is joined to the α-ketoimidomethyl blocking group; and
  Y is hydrogen or one or more substituents selected from the group consisting of halogen, nitro, alkyl, aryl, alkenyl, alkoxy, aryloxy, alkenyloxy, alkylcarbonyl, arylcarbonyl, alkenylcarbonyl, alkylsulfonyl, arylsulfonyl, alkenylsulfonyl, amino, aminocarbonyl, aminosulfonyl, carboxy, alkoxycarbonyl, aryloxycarbonyl and alkenyloxycarbonyl.

16. A photographic element of any one of claims 13 or 14 wherein the α-ketoimidomethyl blocked photographic reagent has the structure:

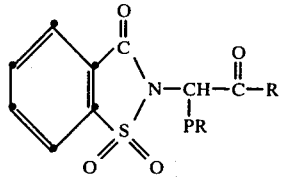

wherein:
  R represents aryl of 6 to 30 carbon atoms; and
  PR represents the residue of a development inhibitor containing a sulfur or nitrogen atom through which it is joined to the α-ketoimidomethyl blocking group.

17. An image transfer cover sheet element capable of being permeated by an alkaline processing composition, comprising a support having thereon a neutralizing layer and a timing layer, the element containing an α-ketoimidomethyl blocked photographic reagent having the structure:

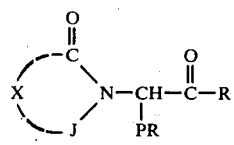

wherein:
J represents

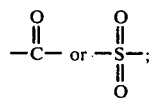

X represents the atoms to complete a heterocyclic nucleus containing at least one 5- or 6-membered ring;

R represents alkyl of 1 to 30 carbon atoms or aryl of 6 to 30 carbon atoms; and

PR represents the residue of a development inhibitor containing a sulfur or nitrogen atom through which it is joined to the α-ketoimidomethyl blocking group.

18. A cover sheet element of claim 17 wherein the α-ketoimidomethyl blocked photographic reagent has one of the structures:

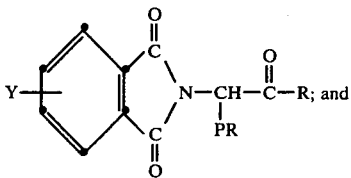

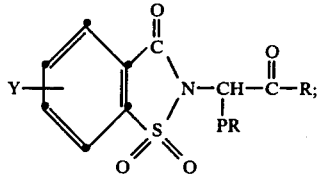

wherein:
  R represents alkyl of 1 to 30 carbon atoms or aryl of 6 to 30 carbon atoms;
  PR represents the residue of a development inhibitor containing a sulfur or nitrogen atom through which it is joined to the α-ketoimidomethyl blocking group; and
  Y is hydrogen or one or more substituents selected from the group consisting of halogen, nitro, alkyl, aryl, alkenyl, alkoxy, aryloxy, alkenyloxy, alkylcarbonyl, arylcarbonyl, alkenylcarbonyl, alkylsulfonyl, arylsulfonyl, alkenylsulfonyl, amino, aminocarbonyl, aminosulfonyl, carboxy, alkoxycarbonyl, aryloxycarbonyl and alkenyloxycarbonyl.

19. A cover sheet element of claim 17 wherein the α-ketoimidomethyl blocked photographic reagent has the structure:

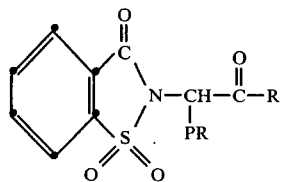

wherein:

R represents aryl of 6 to 30 carbon atoms; and

PR represents the residue of a development inhibitor containing a sulfur or nitrogen atom through which it is joined to the α-ketoimidomethyl blocking group.

20. A cover sheet element of any one of claims 17, 18 or 19 further comprising a dye image receiving layer.

21. A process of forming a photographic image in an imagewise exposed element of any one of claims 1, 2, 13 or 14 comprising contacting the element with an alkaline processing composition to effect development of developable silver halide and to unblock the blocked photographic reagent.

* * * * *